US006465693B2

(12) United States Patent
Buchwald et al.

(10) Patent No.: US 6,465,693 B2
(45) Date of Patent: Oct. 15, 2002

(54) METAL-CATALYZED ARYLATIONS OF HYDRAZINES, HYDRAZONES, AND RELATED SUBSTRATES

(75) Inventors: Stephen L. Buchwald, Newton, MA (US); Seble Wagaw, Cambridge, MA (US); O. Geis, Berlin (DE)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/765,072

(22) Filed: Jan. 18, 2001

(65) Prior Publication Data

US 2001/0031894 A1 Oct. 18, 2001

Related U.S. Application Data

(62) Division of application No. 09/030,936, filed on Feb. 26, 1998, now Pat. No. 6,235,936.

(51) Int. Cl.$^7$ ...................... C07C 209/00; C07C 241/00
(52) U.S. Cl. ...................... 564/386; 564/250; 564/251; 564/389; 564/391; 564/405; 564/407
(58) Field of Search ................................ 564/250, 251, 564/386, 389, 391, 405, 407

(56) References Cited

U.S. PATENT DOCUMENTS

| 3,867,452 A | 2/1975 | Wilcox ........................ 260/569 |
| 4,374,271 A | 2/1983 | Hunter et al. ................ 564/310 |
| 5,576,460 A | 11/1996 | Buchwald et al. |

FOREIGN PATENT DOCUMENTS

| EP | 0 078 768 A1 | 5/1983 |
| EP | 0 187 285 A2 | 7/1986 |
| EP | 0 224 831 A2 | 6/1987 |
| EP | 0 790 233 A2 | 8/1997 |
| WO | WO 95/25090 | * 9/1995 |
| WO | WO 97/41177 | 11/1997 |
| WO | WO 98/06725 | 2/1998 |

OTHER PUBLICATIONS

Barton, H.R. Derek, et al., "Metallic Copper Catalysis of N–Arylation of Amines By Triarylbismuth Diacylates", *Tetraherdon Letters*, vol. 27, No. 31, pp. 3615–3618, (1986).
Cristau, H. J., et al., "Arylation Catalytique D'OrganoPhosphores. Produits De L'Arylation, Catalysee Par Les Sels De Nickel (II), De Composes Du Phosphore Tricoordine", *Journal of Organometallic Chemistry*, 185, pp. 283–295, (1980).
Driver, Michael S., et al., "A Second–Generation Catalyst for Aryl Halide Amination: Mixed Secondary Amines from Aryl Halides and Primary Amines Catalyzed by (DPPF) PdC12", *J. Am. Chem. Soc.*, vol. 118, pp. 7217–7218, (1996).

Goodson, Felix, E., et al., "Regiodefined Poly (N–arylaniline)s and Donor–Acceptor Copolymers via Palladium––Mediated Animation Chemistry", *Macromolecules*, vol. 31, pp. 1700–1703, (1998).
Greiner, Alfred, "An Improvement of the N–Arylation of Amides; Application to the Synthesis of Substituted 3–(N–Acetyl–N–phenylamino)–pyridines", *Synthesis*, pp. 312–313, (Apr. 1989).
Guram, Anil S., et al., "A Simple Catalytic Method for the Conversion of Aryl Bromides to Arylamines", *Angew. Chem. Int. Ed. Engl.* vol. 34, No. 12, (1995).
Hamann, Blake C., et al., "Palladium–Catalyzed Direct a–Arylation of Ketones, Rate Acceleration by Sterically Hindered Chelating Ligands and Reductive Elimination from a transition Metal Enolate Complex", *J. Am. Chem. Soc.*, vol. 119, pp. 12382–12383, (1997).
Kang, Suk–Ku, et al., "Palladium–Catalyzed Synthesis of Arylamines From Diphenyliodonium Tetrafluoroborate and Secondary Amine", *Synthetic Communications*, vol. 26(22), pp. 4219–4224, (1996).
Louie, Janis, et al., "Palladium–Catalyzed Synthesis of Arylamines from Aryl Halides. Mechanistic Studies Lead to Coupling in the Absence of Tin Reagents", *Tetrahedron Letters*, vol. 36, No. 21, pp. 3609–3612, (1995).
Perry, Robert J., et al., "Synthesis of 2–Arylbenzoxazoles via the Palladium–Catalyzed Carbonylation and Condensation of Aromatic Halides and o–Aminophenols", *J. Org. Chem.*, vol. 57, pp. 2883–2887, (1992).
Sonesson, Clas, et al., "Regioselective Synthesis of 3–Aryl Substituted Pyrrolidines Via Palladium Catalyzed Arylation: Pharmacological Evaluation For Central Dopaminergic and Serotoergic Activity", *Bioorganic & Medicinal Chemistry Letters*, vol. 7, No. 3, pp. 241–246, (1997).
Wagaw, S., et al., "The Synthesis of Aminopyridines: A Method Employing Palladium–Catalyzed Carbon–Nitrogen Bond Formation", *J. Org. Chem.*, vol. 61, pp. 7240–7241, (1996).
Wagaw, S., et al., "Palladium–Catalyzed Coupling of Optically Active Amines with Aryl Bromides", *J. Am. Chem. Soc.*, vol. 119, pp. 8451–8458, (1997).
Wolfe, John P., et al., "Improved Functional Group Compatibility in the Palladium–Catalyzed Amination of Aryl Bromides", *Tetrahedron Letters*, vol. 38, No. 36, pp. 6359–6362, (1997).
Wolfe, John P., et al., "Room Temperature Catalytic Amination of Aryl Iodides", *J. Org Chem.*, vol. 62, pp. 6066–6068, (1997).

* cited by examiner

*Primary Examiner*—James O. Wilson
(74) *Attorney, Agent, or Firm*—Dana M. Gordon; Foley Hoag LLP

(57) ABSTRACT

A method is provided for the transition metal-catalyzed arylation, or vinylation, of hydrazines, hydrazones, and the like. Additionally, the invention provides a conceptually novel strategy, the cornerstone of which is the transition metal-catalyzed arylation or vinylation method, for the synthesis of indoles, carbazoles, and the like. The methods and strategies of the invention may be utilized in standard, parallel, and combinatorial synthetic protocols.

20 Claims, No Drawings

METAL-CATALYZED ARYLATIONS OF HYDRAZINES, HYDRAZONES, AND RELATED SUBSTRATES

Related Applications

This application is a division of U.S. patent application Ser. No. 09/030,936, filed Feb. 26, 1998, now U.S. Pat. No. 6,235,936.

Government Support

This invention was made with government support under Grant No. 9421982-CHE awarded by the National Science Foundation. The government has certain rights in the invention.

BACKGROUND OF THE INVENTION

The present invention relates to improved methods for preparing aryl hydrazines, aryl hydrazones, O-aryl hydroxylamines, N-aryl hydroxylamines, O-aryl oximes and the like which are useful intermediates and end products in pharmaceutical and agricultural applications. Certain products of the present invention are utilized in a novel entry into the classical Fischer indole synthesis.

Despite the recent successes with palladium-catalyzed cross-coupling reactions of Ar—X with amines, comparable couplings of aryl halides with hydrazines and the like have not been reported. Existing methods for the conversion of Ar—X to the corresponding aryl hydrazines often require harsh or restrictive reaction conditions and/or the presence of activating groups on the aromatic ring.

Thus there remains a need for an effective method of preparing a wide range of aryl hydrazines and the like under mild conditions and in high yields. There is a further need for an efficient catalytic system with high efficiencies and turnover numbers for the synthesis of these compounds.

SUMMARY OF THE INVENTION

The present invention provides general and attractive routes to a wide range of aryl hydrazines, aryl hydrazones, O-aryl hydroxylamines, N-aryl hydroxylamines, O-aryl oximes and the like. The methods provide several improvements over methods known heretofore, namely, the efficient synthesis of these compounds under mild conditions and in high yields. In particular, the method of the invention may be used in coupling reactions between aryl halides or sulfonates and ketone or aldehyde hydrazones; the products of these coupling reactions provide indoles via the Fischer indole synthesis. In other aspects of the invention, the invention provides a means of synthesizing combinatorial libraries of indoles, carbazoles and the like.

DETAILED DESCRIPTION OF THE INVENTION

Overview

In one aspect of the invention, an aryl hydrazine is prepared by reacting hydrazine, or a substituted hydrazine, or a hydrazide salt, with an activated aromatic compound in the presence of a base and a metal catalyst that includes a Group VIII metal atom such as iron, cobalt, nickel, ruthenium, rhodium, palladium, iridium and platinum; Group 10 metals—platinum, palladium and nickel—are the most preferred metals. The activated aromatic compound comprises an activated substituent, X, which generally is selected from the group comprising halides and sulfonate esters. When the reaction takes place using an hydrazide salt, an additional base may not be required.

In preferred embodiments, the subject synthetic reaction can be characterized by the general reaction scheme shown below:

Scheme 1

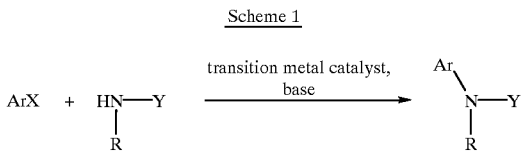

wherein

Ar represents an aromatic group (which may be furthered substituted beyond X);

X represents an activated group (such as a halide or a sulfonate), which can be replaced by a nucleophilic nitrogen in a transition metal-catalyzed arylation reaction;

Y represents $NR_2$, OR, $N=CR_2$, $N(R)S(O)_2R$, or $N(R)C(O)NR_2$;

R represents independently for each occurrence, as valence and stability permit, H, a substituted or unsubstituted alkyl or alkenyl moiety, a formyl, acyl, or sulfonyl moiety, or $—(CH_2)_m—R_8$, $R_8$ represents independently for each occurrence a substituted or unsubstituted aryl, cycloalkyl, cycloalkenyl, heterocycle or polycycle; and m is an integer in the range 0 to 8 inclusive.

In additional preferred embodiments, the subject synthetic reaction can be characterized by the general reaction scheme shown below:

Scheme 2

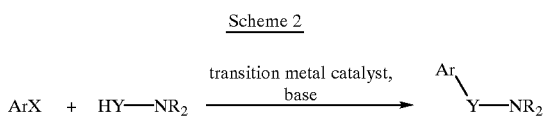

wherein

Ar represents an aromatic group (which may be furthered substituted beyond X);

X represents an activated group (such as a halide or a sulfonate), which can be replaced by a nucleophilic nitrogen in a transition metal-catalyzed arylation reaction;

Y represents O, S, or Se;

R independently for each occurrence is absent or represents, as valence and stability permit, H, a substituted or unsubstituted alkyl or alkenyl moiety, an alkylidene moiety, a formyl, acyl, or sulfonyl moiety, or $—(CH_2)_m—R_8$, $R_8$ represents independently for each occurrence a substituted or unsubstituted aryl, cycloalkyl, cycloalkenyl, heterocycle or polycycle; and m is an integer in the range 0 to 8 inclusive.

In further preferred embodiments, the subject reaction may be an intramolecular reaction. In this instance, it will be realized that, with reference to Scheme 1, YNHR is covalently attached to Ar via T which represents a tether between Ar and Y. The intramolecular reaction results in a product containing at least one more ring than the substrate and said reaction can be represented as follows in Scheme 3:

Scheme 3

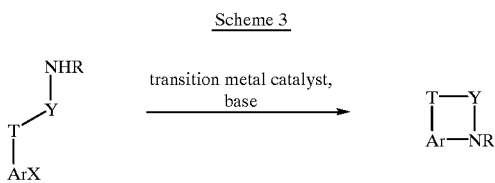

wherein

Ar represents an aromatic group (which may be furthered substituted beyond X and T—Y—NHR);

X represents an activated group (such as a halide or a sulfonate), which can be replaced by a nucleophilic nitrogen in a transition metal-catalyzed arylation reaction;

Y represents NR, O, $sp^2$-hybridized N in a $\pi$-bond to T, $NS(O)_2R$, or $NC(O)NR_2$;

T represents a covalent tether connecting Y and Ar, said tether comprising between 0 and 4 backbone atoms; the backbone of said tether may comprise a $\pi$-bond, provided that the configuration of said $\pi$-bond is such that the described intramolecular reaction is geometrically feasible, or that said $\pi$-bond can adopt a configuration under the reaction conditions that renders the intramolecular reaction geometrically feasible; said tether additionally may itself be either unsubstituted or bear any number of substituents of any type permitted by stability and the rules of valence;

R independently for each occurrence represents, as valence and stability permit, H, a substituted or unsubstituted alkyl or alkenyl moiety, a formyl, acyl, or sulfonyl moiety, or $—(CH_2)_m—R_8$;

$R_8$ represents independently for each occurrence a substituted or unsubstituted aryl, cycloalkyl, cycloalkenyl, heterocycle or polycycle; and m is an integer in the range 0 to 8 inclusive.

In additional preferred embodiments, the subject reaction may be another form of intramolecular reaction. In this instance, it will be realized that, with reference to Scheme 2, N(R)YH is covalently attached to Ar via T which represents a tether between Ar and N. The intramolecular reaction results in a product containing at least one more ring than the substrate and said reaction can be represented as follows in Scheme 4:

Scheme 4

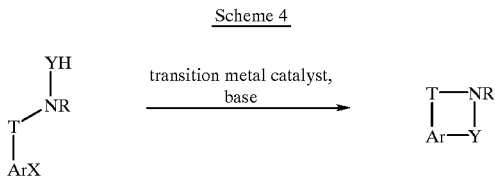

wherein

Ar represents an aromatic group (which may be furthered substituted beyond X and T—NR—YH);

X represents an activated group (such as a halide or a sulfonate), which can be replaced by a nucleophilic nitrogen in a transition metal-catalyzed arylation reaction;

Y represents O, S, or Se;

T represents a covalent tether connecting NR and Ar, said tether comprising between 0 and 4 backbone atoms; the backbone of said tether may comprise a $\pi$-bond, provided that the configuration of said $\pi$-bond is such that the described intramolecular reaction is geometrically feasible, or that said $\pi$-bond can adopt a configuration under the reaction conditions that renders the intramolecular reaction geometrically feasible; said tether additionally may itself be either unsubstituted or bear any number of substituents of any type permitted by stability and the rules of valence;

R represents independently for each occurrence, as valence and stability permit, H, a substituted or unsubstituted alkyl or alkenyl moiety, a formyl, acyl, or sulfonyl moiety, or $—(CH_2)_m—R_8$;

$R_8$ represents independently for each occurrence a substituted or unsubstituted aryl, cycloalkyl, cycloalkenyl, heterocycle or polycycle; and m is an integer in the range 0 to 8 inclusive.

In another embodiment, the subject synthetic reaction can be characterized by the general reaction scheme shown below in Scheme 5:

Scheme 5

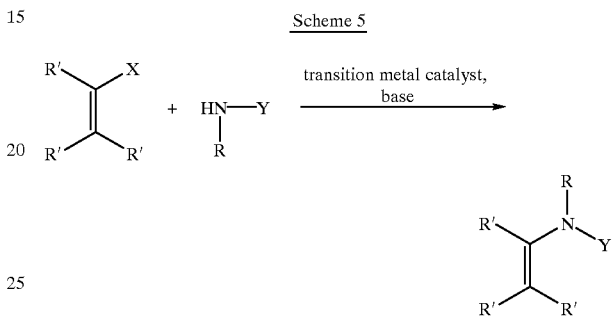

wherein

X represents an activated group (such as a halide or a sulfonate), which can be replaced by a nucleophilic nitrogen in a transition metal-catalyzed vinylation reaction;

Y represents $NR_2$, OR, $N=CR_2$, $N(R)S(O)_2R$, or $N(R)C(O)NR_2$;

R represents independently for each occurrence, as valence and stability permit, H, a substituted or unsubstituted alkyl or alkenyl moiety, a formyl, acyl, or sulfonyl moiety, or $—(CH_2)_m—R_8$;

R' represents independently for each occurrence, as valence and stability permit, H, halogen, lower alkyl, lower alkenyl, lower alkynyl, carbonyl group (e.g. ester, carboxylate, or formate), thiocarbonyl (e.g. thiolester, thiolcarboxylate, or thiolformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, $—(CH_2)_m—R_8$, $—(CH_2)_m—OH$, $—(CH_2)_m—O$-lower alkyl, $—(CH_2)_m—O$-lower alkenyl, $—(CH_2)_m—O—(CH_2)_n—R_8$, $—(CH_2)_m—SH$, $—(CH_2)_m—S$-lower alkyl, $—(CH_2)_m—S$-lower alkenyl, $—(CH_2)_m—S—(CH_2)_n—R_8$, or protecting groups of the above, or a solid or polymeric support;

$R_8$ represents independently for each occurrence a substituted or unsubstituted aryl, cycloalkyl, cycloalkenyl, heterocycle or polycycle; and n and m are integers independently for each occurrence selected from the range of 0 to 8 inclusive.

In yet another embodiment, the subject synthetic reaction can be characterized by the general reaction scheme shown below in Scheme 6:

Scheme 6

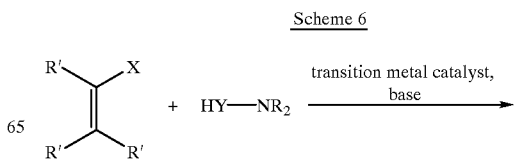

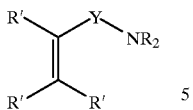

wherein

X represents an activated group (such as a halide or a sulfonate), which can be replaced by a nucleophilic nitrogen in a transition metal-catalyzed vinylation reaction;

Y represents O, S, or Se;

R independently for each occurrence is absent or represents, as valence and stability permit, H, a substituted or unsubstituted alkyl or alkenyl moiety, an alkylidene moiety, a formyl, acyl, or sulfonyl moiety, or —$(CH_2)_m$—$R_8$;

R' represents independently for each occurrence, as valence and stability permit, H, halogen, lower alkyl, lower alkenyl, lower alkynyl, carbonyl group (e.g. ester, carboxylate, or formate), thiocarbonyl (e.g. thiolester, thiolcarboxylate, or thiolformate), ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, —$(CH_2)_m$—$R_8$, —$(CH_2)_m$—OH, —$(CH_2)_m$—O-lower alkyl, —$(CH_2)_m$—O-lower alkenyl, —$(CH_2)_m$—O—$(CH_2)_n$—$R_8$, —$(CH_2)_m$—SH, —$(CH_2)_m$—S-lower alkyl, —$(CH_2)_m$—S-lower alkenyl, —$(CH_2)_m$—S—$(CH_2)_n$—$R_8$, or protecting groups of the above, or a solid or polymeric support;

$R_8$ represents independently for each occurrence a substituted or unsubstituted aryl, cycloalkyl, cycloalkenyl, heterocycle or polycycle; and n and m are integers independently for each occurrence selected from the range of 0 to 8 inclusive.

Artisans of ordinary skill will recognize the potential for intramolecular variants of the vinylation reactions presented in Schemes 5 and 6. Specifically, a comparison of the embodiment of the subject method depicted in Scheme 1 with that in Scheme 3, and a similar comparison of the embodiments depicted in Schemes 2 and 4, will serve to teach the embodiments that comprise an intramolecular vinylation reaction.

While not being bound by any particular mode of operation, it is hypothesized that the mechanism of the preferred Pd-catalyzed arylation of hydrazines and the like may proceed via a pathway similar to that depicted in Scheme 7. Scheme 7 presents a proposed reaction pathway for the synthesis of an aryl hydrazine via an intermolecular reaction. Any ligands that may be present on the palladium atom during this process have been omitted for clarity. With reference to Scheme 7, oxidative addition of the Pd(0) complex to the C—X bond of the activated aryl moiety (ArX) affords the Pd(II) organometallic intermediate A. The hydrazine could then displace X⁻ from A and thereby generate cation B. Cation B would then suffer deprotonation to afford charge neutral intermediate C, which would subsequently undergo reductive elimination to yield the product aryl hydrazine and regenerate the active catalyst. The reaction sequence is likely to be similar for intramolecular reactions. Alternatively, and particularly for nickel catalysts, the active transition metal species in the oxidative addition step may involve the metal in the +1 oxidation state.

Scheme 7

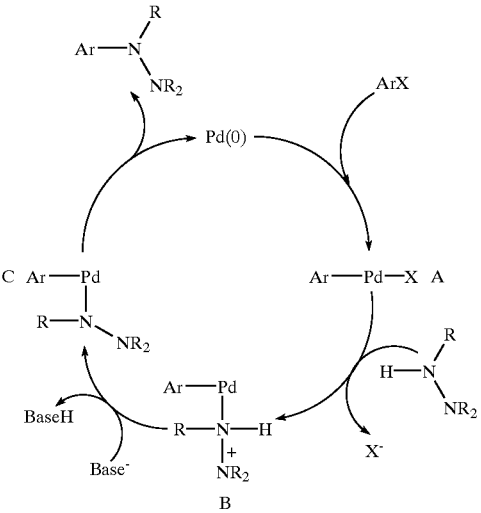

In preferred embodiments of the invention, there is no need to use large excesses of either reactant—hydrazine and the like or aromatic compound. The reaction proceeds quickly and in high yield to the reaction product using substantially stoichiometric amounts of reagents. Thus, the hydrazine may be present in as little as a two-fold excess and preferably in no greater than a 20% excess relative to the aromatic compound. Alternatively, the aromatic compound may be present in as little as a two-fold excess and preferably in no greater than a 20% excess relative to the hydrazine.

The reaction can proceed at mild temperatures and pressures to give high yields of the product aryl hydrazine or the like. Thus, yields of greater than 45%, preferably greater than 75% and even more preferably greater than 80% may be obtained by reaction at mild temperatures according to the invention. The reaction may be carried out at temperature less than 120° C., and preferably in the range of 50–120° C. In one preferred embodiment, the reaction is carried out at a temperature in the range of 80–100° C.

The reaction can be run in a wide range of solvent systems, including polar aprotic solvents. Alternatively, in certain embodiments, the subject reactions may be carried in the absence of added solvent.

The ability to provide a synthesis scheme for hydrazines and the like which can be carried out under mild conditions and/or with non-polar solvents has broad application, especially in the agricultural and pharmaceutical industries, as well as in the polymer industry. In this regard, the subject reaction is more amenable to use of reactants or products which include sensitive functionalities, e.g., which would otherwise be labile under harsh reaction conditions.

The subject hydrazine arylation reactions can be used as part of a combinatorial synthesis scheme to yield libraries of aryl hydrazines and the like. Accordingly, another aspect of the present invention relates to use of the subject method to generate variegated libraries of aryl hydrazines and the like, and to the libraries themselves. The libraries can be soluble or linked to insoluble supports, e.g., either through substituents of the aryl group or the hydrazine etc.

Definitions

For convenience, before further description of the present invention, certain terms employed in the specification, examples, and appended claims are collected here.

The term "substrate aryl group" refers to an aryl group containing an electrophilic atom which is susceptible to the subject cross-coupling reaction, e.g., the electrophilic atom bears a leaving group. In reaction scheme 1, the substrate aryl is represented by ArX, and X is the leaving group. The aryl group, Ar, is said to be substituted if, in addition to X, it is substituted at yet other positions. The substrate aryl group can be a single ring molecule, or can be a component of a larger molecule.

The terms "hydrazine and/or the like" refer to a hydrazine, hydrazone, hydroxylamine, oxime etc. which can attack the electrophilic atom of the substrate aryl group and displace the leaving group in the subject cross-coupling reaction. In Schemes 1 and 2, the nucleophilic hydrazine and/or the like are represented by HN(R)—Y, and HY—NR$_2$, respectively. The hydrazine and/or the like can be a component of a molecule separate from the substrate aryl group, or a substituent of the same molecule (e.g., for intramolecular cross couplings).

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above. Electrophilic moieties useful in the method of the present invention include halides and sulfonates.

The terms "electrophilic atom", "electrophilic center" and "reactive center" as used herein refer to the atom of the substrate aryl moiety which is attacked by, and forms a new bond to the nucleophilic heteroatom of the hydrazine and the like. In most (but not all) cases, this will also be the aryl ring atom from which the leaving group departs.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (s) constant. This well known constant is described in many references, for instance, J. March, *Advanced Organic Chemistry*, McGraw Hill Book Company, New York, (1977 edition) pp. 251–259. The Hammett constant values are generally negative for electron donating groups (s[P]=−0.66 for NH$_2$) and positive for electron withdrawing groups (s[P]=0.78 for a nitro group), s[P] indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "reaction product" means a compound which results from the reaction of the hydrazine or the like and the substrate aryl group. In general, the term "reaction product" will be used herein to refer to a stable, isolable aryl ether adduct, and not to unstable intermediates or transition states.

The term "catalytic amount" is recognized in the art and means a substoichiometric amount of reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thiolformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, iamido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry;* this list is typically presented in a table entitled *Standard List of Abbreviations.* The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art recognized and refer to both unsubstituted and substituted amines, e.g., a moiety that can be represented by the general formula:

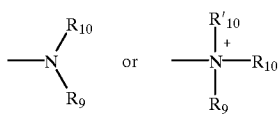

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

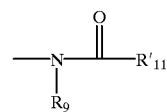

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

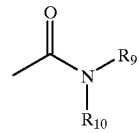

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

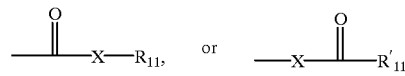

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester".

Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

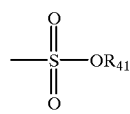

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "sulfate" is art recognized and includes a moiety that can be represented by the general formula:

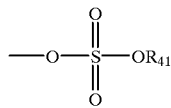

in which $R_{41}$ is as defined above.

The term "sulfonamido" is art recognized and includes a moiety that can be represented by the general formula:

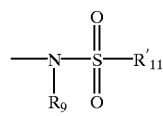

in which $R_9$ and $R'_{11}$ are as defined above.

The term "sulfamoyl" is art-recognized and includes a moiety that can be represented by the general formula:

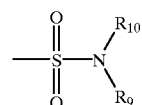

in which $R_9$ and $R_{10}$ are as defined above.

The terms "sulfoxido" or "sulfinyl", as used herein, refers to a moiety that can be represented by the general formula:

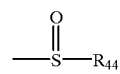

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

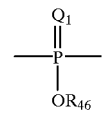

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

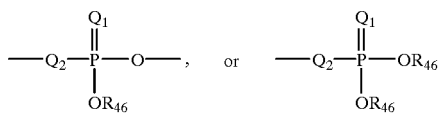

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

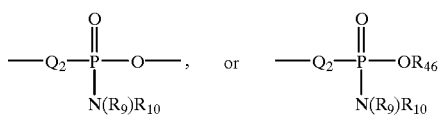

wherein $R_9$ and $R_{10}$ are as defined above, and $Q_2$ represents O, S or N.

A "phosphoramidite" can be represented in the general formula:

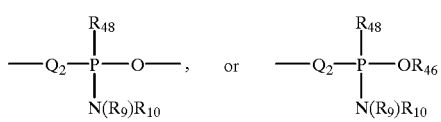

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R$_8$, m and R$_8$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

A "polar solvent" means a solvent which has a dipole moment ($\epsilon$) of 2.9 or greater, such as DMF, THF, ethylene gylcol dimethyl ether, DMSO, acetone, acetonitrile, methanol, ethanol, isopropanol, n-propanol, t-butanol or 2-methoxyethyl ether. Preferred solvents are DMF, diglyme, and acetonitrile.

A "polar, aprotic solvent" means a polar solvent as defined above which has no available hydrogens to exchange with the compounds of this invention during reaction, for example DMF, acetonitrile, diglyme, DMSO, or THF.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

II. Exemplary Catalyzed Reactions

As described above, one invention of the Applicants' features a transition metal-catalyzed cross-coupling reaction which comprises combining a hydrazine with an aryl group (a "substrate aryl") bearing an activated group X. The reaction includes at least a catalytic amount of a transition metal catalyst and the combination is maintained under conditions appropriate for the metal catalyst to catalyze the nucleophilic addition of the reactive hydrazine to the electrophilic atom of the substrate aryl.

In an illustrative embodiment, the subject method can be used for the intermolecular reaction between an activated aryl substrate and a hydrazine to give an aryl hydrazine:

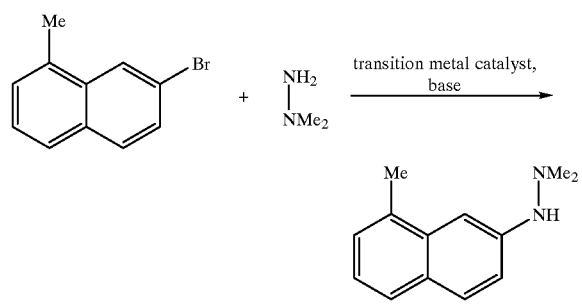

In a second illustrative embodiment, the subject method can be used to bring about an intramolecular arylation of a hydrazine; said arylation yields a diazaheterocycle. In some cases, including the case illustrated below, the initially-formed diazaheterocycle can be oxidized to yield a new diazaaromatic compound:

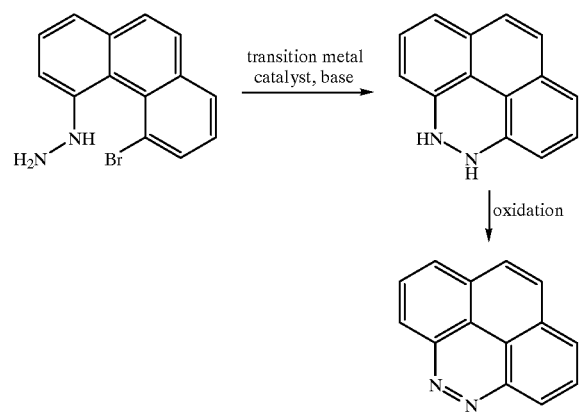

Another aspect of the Applicants' invention features a transition metal-catalyzed cross-coupling reaction which comprises combining a hydroxylamine with an aryl group (a "substrate aryl") being an activated group X. The reaction includes at least a catalytic amount of a transition metal catalyst and the combination is maintained under conditions appropriate for the metal catalyst to catalyze the nucleophilic addition of a reactive nitrogen or oxygen of a hydroxylamine, depending upon substrates and conditions selected, or a reactive oxygen of an oxime to the electrophilic atom of the substrate aryl.

In an embodiment illustrative of this aspect of the invention, the subject method can be exploited for the preparation of an O-alkenyl oxime from a vinyl halide and an oxime:

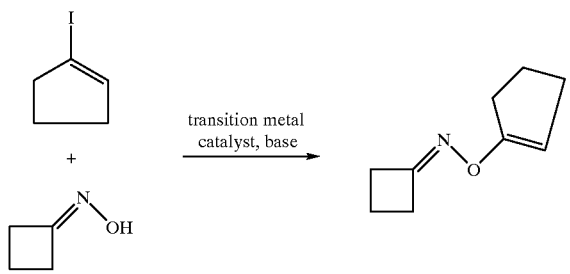

In an second embodiment illustrative of this aspect of the invention, the subject method can be exploited in the arylation of an O-alkyl hydroxylamine to give an N-aryl-O-alkyl hydroxylamine:

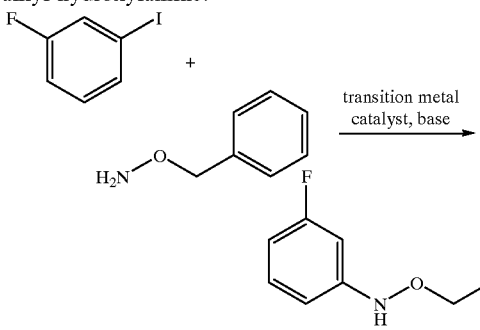

Intramolecular variants are available of the aspects of the invention that center on hydroxyl amines. An illustrative embodiment is shown below:

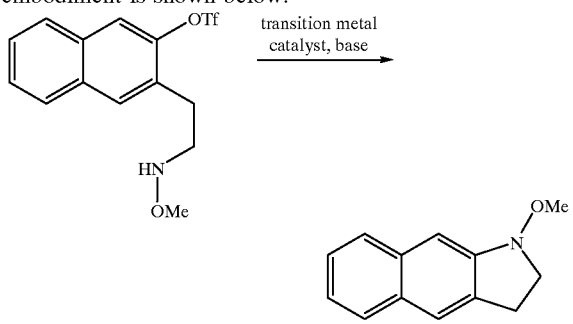

A second illustrative embodiment of an intramolecular arylation of a hydroxyl amine is shown below. Also illustrated below is the potential for the preparation of 1,n-amino alcohols via a subsequent reduction of the nitrogen-oxygen single bond in products of the subject arylation.

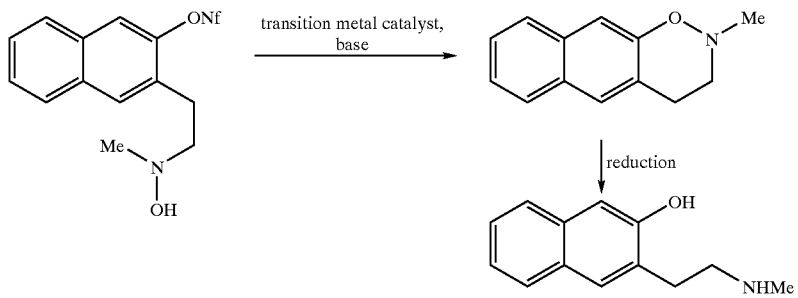

The subject method can be applied to the synthesis of N-arylhydrazones. A preferred embodiment, illustrated below, involves the transition metal catalyzed arylation of benzophenone hydrazone:

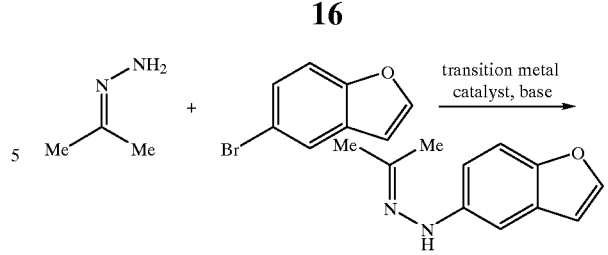

In still another illustrative embodiment, the subject reaction between a hydrazone and an activated aryl substrate, followed by reduction of the resulting N-aryl hydrazone, can be utilized for the synthesis of anilines:

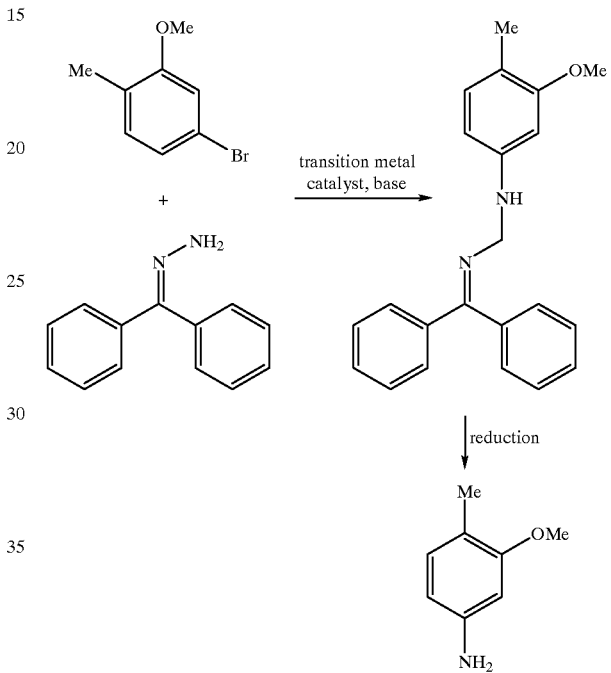

In a highly preferred illustrative embodiment, the subject arylation of benzophenone hydrazone is the initial step in a conceptually novel entry into the Fischer indole synthesis. The entire sequence of events in this novel strategy for indole synthesis is illustrated below. The second step in this strategy involves two discrete events: 1) an acid-catalyzed exchange of a new aldehyde or ketone for benzophenone to form a new hydrazone—labeled "not isolated"—and benzophenone (not shown); and 2) the acid-catalyzed formation of an indole from the second hydrazone via what is known in the art as the Fischer Indole synthesis:

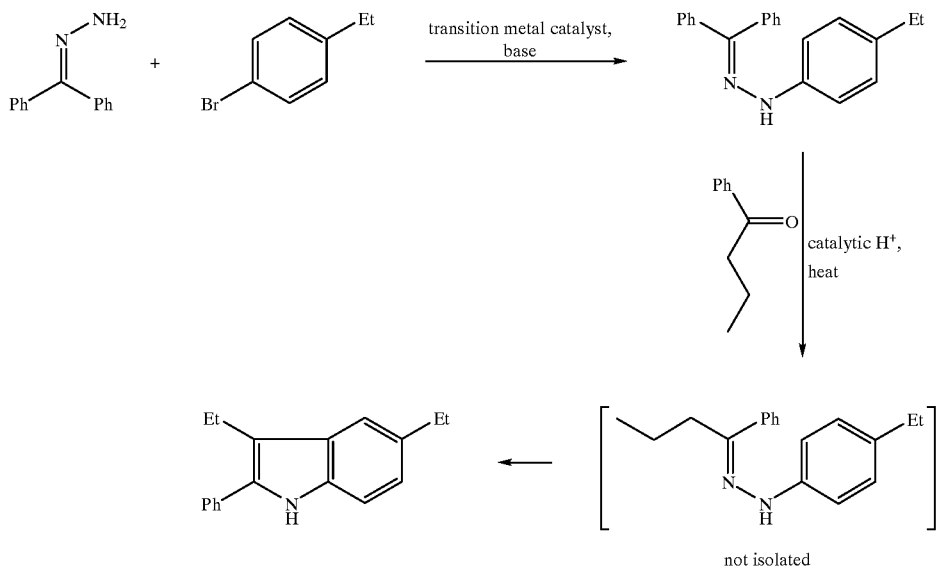

In another highly preferred illustrative embodiment, the subject arylation of benzophenone hydrazone is followed by a second subject arylation to give an N,N-diaryl benzophenone hydrazone. The subsequent step of this embodiment is the acid-catalyzed "exchange in" of a new carbonyl component to produce benzophenone and a new hydrazone (refer to the teachings of the preceding illustrative example); the new hydrazone then undergoes an acid-catalyzed Fischer indole synthesis reaction to give the product indole. The Fischer indole synthesis step in this embodiment is highly selective; the more electron-rich aryl moiety of the intermediate N,N-diaryl hydrazone is selectively incorporated into the indole nucleus of the product, and the less electron-rich aryl moiety appears as a substituent at the 1-position of the indole product.

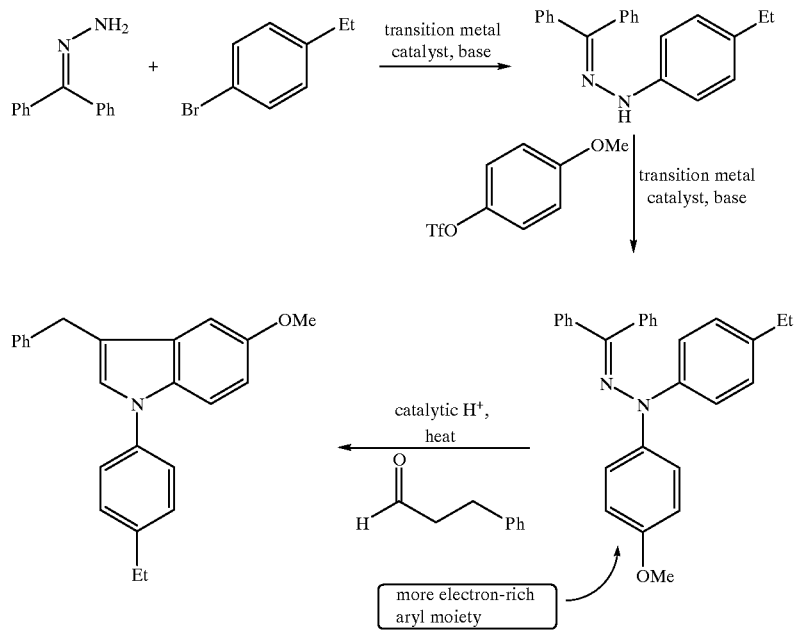

In an additional highly preferred embodiment, the arylation-Fischer Indole synthesis strategy is carried out on a solid support:
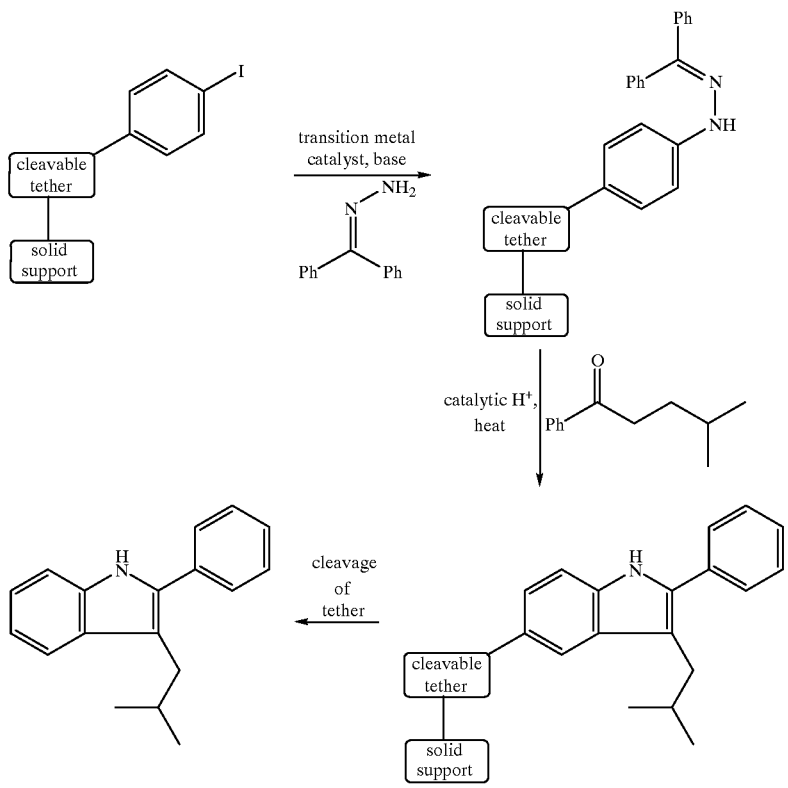
In a further highly preferred embodiment, a combinatorial approach to the arylation-Fischer Indole synthesis strategy on a solid support is pursued to yield a library of indoles:
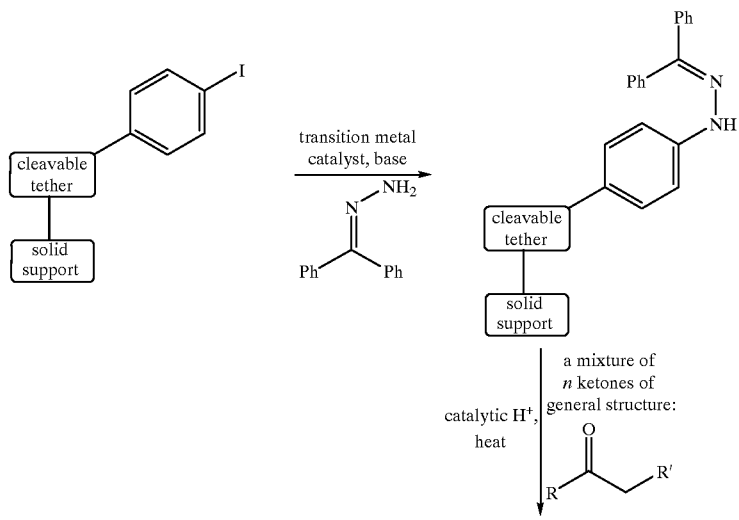

-continued

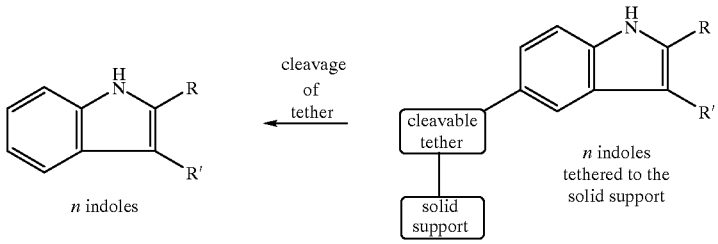

In another highly preferred embodiment, the subject arylation of an oxime can be followed by a step analogous to the Fischer indole synthesis to provide a benzofuran:

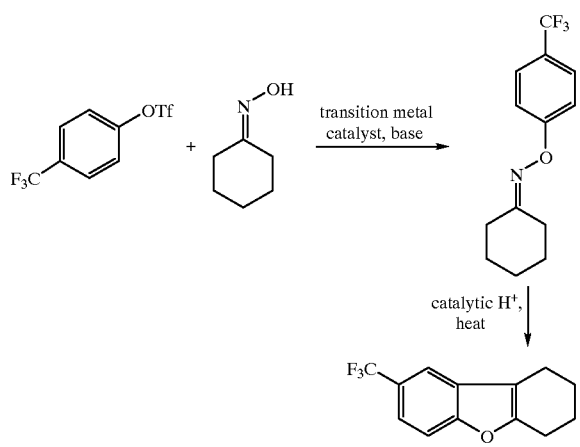

In a highly preferred embodiment, the subject vinylation of a hydrazone can be followed by a step analogous to the Fischer indole synthesis to provide a pyrrole:

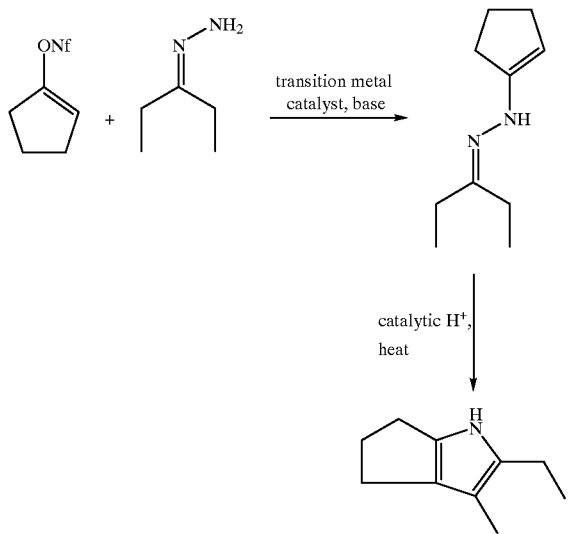

The substrate aryl compounds include compounds derived from simple aromatic rings (single or polycylic) such as benzene, naphthalene, anthracene and phenanthrene; or heteroaromatic rings (single or polycyclic), such as pyrrole, thiophene, thianthrene, furan, pyran, isobenzofluran, chromene, xanthene, phenoxathiin, pyrrole, imidazole, pyrazole, thiazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine and the like. In preferred embodiment, the reactive group, X, is substituted on a five, six or seven membered ring (though it can be part of a larger polycyle).

In preferred embodiments, the aryl substrate may be selected from the group consisting of phenyl and phenyl derivatives, heteroaromatic compounds, polycyclic aromatic and heteroaromatic compounds, and functionalized derivatives thereof. Suitable aromatic compounds derived from simple aromatic rings and heteroaromatic rings, include but are not limited to, pyridine, imidazole, quinoline, furan, pyrrole, thiophene, and the like. Suitable aromatic compounds derived from fused ring systems, include but are not limited to naphthalene, anthracene, tetralin, indole and the like.

Suitable aromatic compounds may have the formula $Z_pArX$, where X is an activated substituent. An activated substituent, X, is characterized as being a good leaving group. In general, the leaving group is a group such as a halide or sulfonate. For the purposes of the present invention, an activated substituent is that moiety whose conjugate acid, HX, has a pKa of less than 5.0. Suitable activated substituents include, by way of example only, halides such as chloride, bromide and iodide, and sulfonate esters such as triflate, mesylate, nonaflate and tosylate. In certain embodiments, the leaving group is a halide selected from iodine and bromine. Chlorine and fluorine can also be used as leaving groups, though other electronegative substitution on the aryl group may be required to activate those halogens as leaving groups in the subject metal cross-coupling reactions.

Z represents one or more optional substituents on the aromatic ring, though each occurence of Z (p>1) is independently selected. By way of example only, each incidence of substitution independently can be, as valence and stability permit, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —$(CH_2)_m$—$R_8$, —$(CH_2)_m$—OH, —$(CH_2)_m$—O-lower alkyl, —$(CH_2)_m$—O-lower alkenyl, —$(CH_2)_m$—

O—$(CH_2)_n$—$R_8$, —$(CH_2)_m$—SH, —$(CH_2)_m$—S-lower alkyl, —$(CH_2)_m$—S-lower alkenyl, —$(CH_2)_m$—S—$(CH_2)_n$—$R_8$, or protecting groups of the above or a solid or polymeric support; $R_8$ represents a substituted or unsubstituted aryl, aralkyl, cycloalkyl, cycloalkenyl, or heterocycle; and n and m are independently for each occurrence zero or an integer in the range of 1 to 6. P is preferably in the range of 0 to 5. For fused rings, where the number of substitution sites on the aryl group increases, p may be adjusted appropriately.

In certain embodiments, suitable substituents Z include alkyl, aryl, acyl, heteroaryl, amino, carboxylic ester, carboxylic acid, hydrogen group, ether, thioether, amide, carboxamide, nitro, phosphonic acid, hydroxyl, sulfonic acid, halide, pseudohalide groups, and substituted derivatives thereof, and p is in the range of 0 to 5. In particular, the reaction has been found compatible with acetals, amides and silyl ethers as functional groups. For fused rings, where the number of substitution sites on the aromatic ring increases, p may be adjusted appropriately. In addition, the above mentioned moieties may be covalently linked to an alcohol moiety in intramolecular reactions.

In preferred embodiments, the resonance structure of the aryl group Ar, or at least one substituent Z, is electron-withdrawing from the substituted position of X.

A wide variety of substrate aryl groups are useful in the methods of the present invention. The choice of substrate will depend on factors such as the hydrazine or the like to be employed and the desired product, and an appropriate aryl substrate will be apparent to the skilled artisan. It will be understood that the aryl substrate preferably will not contain any interfering functionalities. It will further be understood that not all activated aryl substrates will react with every alcohol.

The reactive hydrazine group or the like can be a molecule separate from the substrate aryl group, or a substituent of the same molecule (e.g., for intramolecular condensation).

The hydrazine or the like is selected to provide the desired reaction product. In general, the hydrazine or the like may be selected from the set comprising hydrazines, hydrazones, hydroxylamines and the like. The hydrazine or the like may be functionalized. The hydrazine or the like may be selected from a wide variety of structural types, including but not limited to, acyclic, cyclic or heterocyclic compounds, fused ring compounds or phenol derivatives. The aromatic compound and the hydrazine or the like may be included as moieties of a single molecule, whereby the arylation reaction proceeds as an intramolecular reaction.

In certain embodiments, the reactive hydrazine group or the like which is used in the subject coupling reaction can be represented by general formula RHN—Y or HY—$NR_2$. R represents, as valence and stability permit, a substituted or unsubstituted alkyl or alkenyl group, or —$(CH_2)_m$—$R_8$, wherein $R_8$ represents a substituted or unsubstituted aryl, cycloalkyl, cycloalkenyl, heterocycle or polycycle, and m is zero or an integer in the range of 1 to 8. In other embodiments, R is linker to a solid support.

In certain embodiments, the hydrazine or the like is generated in situ by conversion of a precursor under the reaction conditions, e.g. by deprotonation of a hydrohalide salt of the hydrazine or the like.

Alternatively, the corresponding hydrazide or the like salt, e.g., NaN(R)—Y, LiN(R)—Y, KN(R)—Y, NaY—$NR_2$, LiY—$NR_2$, KY—$NR_2$, etc., may be prepared and used in place of the hydrazine or the like. When the corresponding hydrazide or the like is used in the reaction, an additional base may not be required.

The active form of the transition metal catalyst is not well characterized. Therefore, it is contemplated that the "transition metal catalyst" of the present invention, as that term is used herein, shall include any catalytic transition metal and/or catalyst precursor as it is introduced into the reaction vessel and which is, if necessary, converted in situ into the active form, as well as the active form of the catalyst which participates in the reaction.

In preferred embodiments, the transition metal catalyst complex is provided in the reaction mixture is a catalytic amount. In certain embodiments, that amount is in the range of 0.0001 to 20 mol %, and preferably 0.05 to 5 mol %, and most preferably 1–3 mol %, with respect to the limiting reagent, which may be either the aromatic compound or the hydrazine or the like (or corresponding hydrazide etc.) or both, depending upon which reagent is in stoichiometric excess. In the instance where the molecular formula of the catalyst complex includes more than one metal, the amount of the catalyst complex used in the reaction may be adjusted accordingly. By way of example, $Pd_2(dba)_3$ has two metal centers; and thus the molar amount of $Pd_2(dba)_3$ used in the reaction may be halved without sacrifice to catalytic activity.

Additionally, heterogeneous catalysts containing forms of these elements are also suitable catalysts for any of the transition metal catalyzed reactions of the present invention. Catalysts containing palladium and nickel are preferred. It is expected that these catalysts will perform similarly because they are known to undergo similar reactions, namely oxidative-addition reactions and reductive-elimination reactions, which are thought to be involved in the formation of the aryl hydrazines etc. of the present invention. However, the different ligands are thought to modify the catalyst performance by, for example, modifying reactivity and preventing undesirable side reactions.

As suitable, the catalysts employed in the subject method involve the use of metals which can mediate cross-coupling of the aryl groups ArX and the hydrazine or the like as defined above. In general, any transition metal (e.g., having d electrons) may be used to form the catalyst, e.g., a metal selected from one of Groups 3–12 of the periodic table or from the lanthanide series. However, in preferred embodiments, the metal will be selected from the group of late transition metals, e.g. preferably from Groups 5–12 and even more preferably Groups 7–11. For example, suitable metals include platinum, palladium, iron, nickel, ruthenium and rhodium. The particular form of the metal to be used in the reaction is selected to provide, under the reaction conditions, metal centers which are coordinately unsaturated and not in their highest oxidation state. The metal core of the catalyst should be a zero valent transition metal, such as Pd or Ni with the ability to undergo oxidative addition to Ar–X bond. The zero-valent state, $M^0$, may be generated in situ from $M^{+2}$.

To further illustrate, suitable transition metal catalysts include soluble or insoluble complexes of platinum, palladium and nickel. Nickel and palladium are particularly preferred and palladium is most preferred. A zero-valent metal center is presumed to participate in the catalytic carbon-heteroatom bond forming sequence. Thus, the metal center is desirably in the zero-valent state or is capable of being reduced to metal(0). Suitable soluble palladium complexes include, but are not limited to, tris (dibenzylideneacetone) dipalladium [$Pd_2(dba)_3$], bis (dibenzylideneacetone) palladium [$Pd(dba)_2$] and palladium acetate. Suitable catalysts for a heterogeneous arylation reaction include, but are not limited to, palladium on carbon (Pd/C). Alternatively, particularly for nickel catalysts, the active species for the oxidative-addition step may be in the metal (+1) oxidative-addition state.

Catalysts containing palladium and nickel are preferred. It is expected that these catalysts will perform comparably because they are known to undergo similar reactions, namely cross-coupling reactions, which may be involved in the formation of the aryl hydrazines etc. of the present invention.

The coupling can be catalyzed by a palladium catalyst which may take the form of, to illustrate, $PdCl_2$, $Pd(OAc)_2$, $(CH_3CN)_2PdCl_2$, $Pd[P(C_6H_5)_3]_4$, and polymer supported Pd(0). In other embodiments, the reaction can be catalyzed by a nickel catalyst, such as $Ni(acac)_2$, $NiCl_2[P(C_6H_5)]_2$, $Ni(1,5\text{-cyclooctadiene})_2$, $Ni(1,10\text{-phenanthroline})_2$, $Ni(dppf)_2$, $NiC_2(dppf)$, $NiCl_2(1,10\text{-phenanthroline})$, Raney nickel and the like, wherein "acac" represents acetylacetonate.

The catalyst will preferably be provided in the reaction mixture as metal-ligand complex comprising a bound supporting ligand, that is, a metal-supporting ligand complex. The ligand effects can be key to favoring, inter alia, the reductive elimination pathway or the like which produces the hydrazine or the like, over such side reactions as β-hydride elimination. In particular, the use of bulky and less electron-donating ligands (but probably still chelating ligands) should favor the reductive elimination process. In preferred embodiments, the subject reaction employs bulky bidentate ligands such as bisphosphines.

The ligand, as described in greater detail below, may include chelating ligands, such as by way of example only, alkyl and aryl derivatives of phosphines and bisphosphines, amines, diamines, imines, arsines, and hybrids thereof, including hybrids of phosphines with amines. Weakly or non-nucleophilic stabilizing ions are preferred to avoid complicating side reaction of the counter ion attacking or adding to the electrophilic center of the substrate aryl. This catalyst complex may include additional ligands as is necessary to obtain a stable complex. Moreover, the ligand can be added to the reaction mixture in the form of a metal complex, or added as a separate reagent relative to the addition of the metal. By way of example, $PdC_2(BINAP)$ may be prepared in a separate step and used as the catalyst complex set forth in Schemes 1–7.

The ligand, if chiral can be provided as a racemic mixture or a purified stereoisomer.

The supporting ligand may be added to the reaction solution as a separate compound or it may be complexed to the metal center to form a metal-supporting ligand complex prior to its introduction into the reaction solution. Supporting ligands are compounds added to the reaction solution which are capable of binding to the catalyst metal center, although an actual metal-supporting ligand complex has not been identified in each and every synthesis. In some preferred embodiments, the supporting ligand is a chelating ligand. Although not bound by any theory of operation, it is hypothesized that the supporting ligands prevent unwanted side reactions as well as enhancing the rate and efficiency of the desired process. Additionally, they typically prevent precipitation of the catalytic transition metal. Although the present invention does not require the formation of a metal-supporting ligand complex, such complexes have been shown to be consistent with the postulate that they are intermediates in these reactions and it has been observed the selection of the supporting ligand has an affect on the course of the reaction.

The supporting ligand is present in the range of 0.0001 to 40 mol% relative to the limiting reagent, i.e., hydrazine etc.

or aromatic compound. The ratio of the supporting ligand to catalyst complex is typically in the range of about 1 to 20, and preferably in the range of about 1 to 4 and most preferably 2. These ratios are based upon a single metal complex and a single binding site ligand. In instances where the ligand contains additional binding sites (i.e., a chelating ligand) or the catalyst contains more than one metal, the ratio is adjusted accordingly. By way of example, the supporting ligand BINAP contains two coordinating phosphorus atoms and thus the ratio of BINAP to catalyst is adjusted downward to about 1 to 10, preferably about 1 to 2 and most preferably 1. Conversely, $Pd_2(dba)_3$ contains two palladium metal centers and the ratio of a non-chelating ligand to $Pd_2(dba)_3$ is adjusted upward to 1 to 40, preferably 1 to 8 and most preferably 4.

In certain embodiments of the subject method, the transition metal catalyst includes one or more phosphine ligands, e.g., as a Lewis basic ligand that controls the stability and electron transfer properties of the transition metal catalyst, and/or stabilizes the metal intermediates. Phosphine ligands are commercially available or can be prepared by methods similar to processes known per se. The phosphines can be monodentate phosphine ligands, such as trimethylphosphine, triethylphosphine, tripropylphosphine, triisopropylphosphine, tributylphosphine, tricyclohexylphosphine, trimethyl phosphite, triethyl phosphite, tripropyl phosphite, triisopropyl phosphite, tributyl phosphite and tricyclohexyl phosphite, in particular triphenylphosphine, tri(o-tolyl)phosphine, triisopropylphosphine or tricyclohexylphosphine; or a bidentate phosphine ligand such as 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino) ethane, 1,2-bis(diisopropylphosphino)ethane, 1,2-bis(dibutyl-phosphino)ethane, 1,2-bis(dicyclohexylphosphino) ethane, 1,3-bis(dicyclohexylphosphino)propane, 1,3-bis (diiso-propylphosphino)propane, 1,4-bis (diisopropylphosphino)-butane and 2,4-bis (dicyclohexylphosphino)pentane.

In preferred embodiments, the phosphine ligand is one (or a mix of) of $P(o\text{-tolyl})_3$. Bis(phosphine) ligands are particularly preferred chelating supporting ligands. Suitable bis (phosphine) compounds include but are in no way limited to (±)-2,2'-bis(diphenylphosphino)-1,1'-binaphthyl (and separate enantiomers), (±)-2,2'-bis(di-p-tolylphosphino)-1,1'-binaphthyl (and separate enantiomers), 1–1'-bis (diphenylphosphino)ferrocene (dppf), 1,3-bis (diphenylphosphino)propane (dppp), 1,2-bis (diphenylphosphino)benzene, 2,2'-bis(diphenylphosphino) diphenyl ether, and 1,2-bis(diphenylphosphino)ethane (dppe). Hybrid chelating ligands such as (±)-N,N-dimethyl-1-[2-(diphenylphosphino) ferrocenyl]ethylamine (and separate enantiomers), and (±)-(R)-1-[(S)-2-(diphenylphosphino)-ferrocenyl]ethyl methyl ether (and separate enantiomers) are also within the scope of the invention.

In some instances, it may be necessary to include additional reagents in the reaction to promote reactivity of either the transition metal catalyst or activated aryl nucleus. In particular, it may be advantageous to include a suitable base. In general, a variety of bases may be used in practice of the present invention. It has not been determined if deprotonation occurs prior to or after heteroatom coordination to the transition metal of the active catalyst. The base may optionally be sterically hindered to discourage metal coordination of the base in those circumstances where such coordination is possible, i.e., alkali metal alkoxides. Exemplary bases include such as, for example: an alkoxides such as sodium tert-butoxide, an alkali metal amide such as sodium amide, lithium diisopropylamide or an alkali metal bis(trialkylsilyl) amides, e.g., such as lithium bis(trimethylsilyl)amide or sodium bis(trimethylsilyl) amide, a tertiary amine (e.g. triethylamine, trimethylamine, 4-(dimethylamino)pyridine (DMAP), 1,5-diazabicycl[4.3.0]non-5-ene (DBN), 1,5-diazabicyclo[5.4.0]undec-5-ene (DBU), alkali, alkaline earth carbonate, bicarbonate or hydroxide (e.g. sodium, magnesium, calcium, barium, potassium carbonate, hydroxide and bicarbonate). By way of example only, suitable bases include NaH, LiH, KH, $K_2CO_3$, $Na_2CO_3$, $Tl_2CO_3$, $Cs_2CO_3$, K(OtBu), Li(OtBu), Na(OtBu) K(OPh), Na(OPh), triethylamine or mixtures thereof NaH, Na(OtBu) and $K_2CO_3$ have been found useful in a wide variety of aryl ether bond forming reactions. Preferred bases include $Cs_2CO_3$, DBU, NaH, KOt-Bu, LiN(i-Pr)$_2$ (LDA), $KN(SiMe_3)_2$, $NaN(SiMe_3)_2$, and $LiN(SiMe_3)_2$.

Base is used in approximately stoichiometric proportions in reactions using hydrazines etc. The present invention has demonstrated that there is no need for large excesses of base in order to obtain good yields of aryl hydrazines etc. under mild reaction conditions. No more than four equivalents and preferably no more than two equivalents are needed. Further, in reactions using the corresponding hydrazide etc. as the reagent, there may be no need for additional base.

In this way a wide range of aryl hydrazines, aryl hydrazones, and N- and O-aryl hydroxylamines may be prepared from available hydrazines, hydrazones and hydroxylamines and the corresponding hydrohalide salts. The reaction can be accomplished using a wide range of hydrazines and the like, which are either commercially available or obtainable from conventional syntheses using a variety of methods known in the art.

As is clear from the above discussion, the products which may be produced by the arylation reaction of this invention can undergo further reaction(s) to afford desired derivatives thereof. Such permissible derivatization reactions can be carried out in accordance with conventional procedures known in the art. For example, potential derivatization reactions include esterification, oxidation of alcohols to aldehydes and acids, N-alkylation of amides, nitrile reduction, acylation of alcohols by esters, acylation of amines and the like.

III. Reaction Conditions

The arylation reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants and catalyst. The reactions will usually be run at temperatures in the range of 25° C. to 300° C., more preferably in the range 25° C. to 150° C.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical and may be accomplished in any conventional fashion. In a preferred order of events that leads to an enhancement of the reaction rate, the base, e.g. t-BuONa, is the last ingredient to be added to the reaction mixture.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivativation with one or more of substituents of the aryl group.

IV. Combinatorial Libraries

The subject arylation reaction readily lends itself to the creation of combinatorial libraries of aryl hydrazines, aryl hydrazones, N- and O-aryl hydroxylamines, and indoles for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property is done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject aryl hydrazines etc. and indoles. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers of the subject aryl hydrazines etc. or indoles can be synthesized and screened for particular activity or property.

In an exemplary embodiment, a library of substituted diversomers can be synthesized using the subject cross-coupling reaction adapted to the techniques described in the Still et al. PCT publication WO 94/08051, e.g., being linked to a polymer bead by a hydrolyzable or photolyzable group e.g., located at one of the positions of the aryl group or a substituent of the hydrazine and the like. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay.

Exemplification

The invention may be understood with reference to the following examples, which are presented for illustrative purposes only and which are non-limiting. Hydrazines, hydrazones, ketones and aromatic halides utilized as substrates in these examples were either commercially available or were prepared in three or less steps from commercially available reagents. Palladium catalysts were all commercially available.

EXAMPLE 1

Synthesis of N-Phenyl-N-4-tolyl-N'-trifluoroacetichydrazide

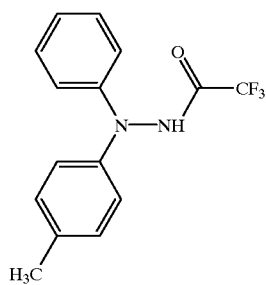

Phenylhydrazine (1.2 equiv., 0.6 mmol, 0.06 mL), 4-bromotoluene (1.0 equiv., 0.5 mmol, 0.06 mL), Pd(OAc)$_2$ (0.05 equiv., 0.025 mmol, 6 mg), BINAP (0.05 equiv., 0.025 mmol, 16 mg), NaOtBu (1.4 equiv., 0.7 mmol, 67 mg) and diisopropylamine (2 mL) were added to an oven dried test tube which was capped with a septum and purged briefly with argon (~1 min.), and then heated to 80° C. under argon for 1 hour. The reaction was then cooled to room temperature, diluted with Et$_2$O (2 mL), filtered through Celite and concentrated under vacuum. Trifluoroacetic anhydride (5 equiv., 2.5 mmol, 0.35 mL), triethylamine (5 equiv., 2.5 mmol, 0.35 mL), and CH$_2$Cl$_2$ were added to the crude reaction mixture and allowed to stir at room temperature for 1 hour. The reaction solution was then washed with a saturated NaHCO$_3$ solution (2×10 mL), dried over MgSO$_4$, filtered and concentrated under vacuum. The crude mixture was purified by flash column chromatography (10% EtOAc/Hex) to give the title product as a white solid (97 mg, 0.35 mmol, 70% yield).

EXAMPLE 2

Synthesis of N-(4-Fluorophenyl)-N-(4-phenylphenyl)hydrazine

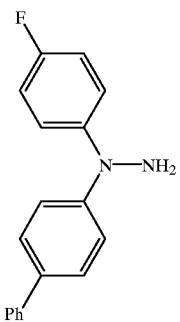

4-Fluorophenylhydrazine hydrochloride (1–2 equiv., 0.6 mmol, 98 mg), 4-bromobiphenyl (1.0 equiv., 0.5 mmol, 117 mg), Pd(OAc)$_2$ (0.05 equiv., 0.025 mmol, 6 mg), BINAP (0.05 equiv., 0.025 mmol, 16 mg), NaOtBu (1.4 equiv., 0.7 mmol, 67 mg) and diisopropylamine (2 mL) were added to an oven dried test tube which was capped with a septum and purged briefly with argon (~1 min.), and then heated to 50° C. under argon for 7 hours. The reaction was then cooled to room temperature, diluted with Et2O (2 mL), filtered through Celite and concentrated under vacuum. The crude mixture was purified by flash column chromatography (10% EtOAc/Hex) to give the title product as a white solid (110 mg, 0.39 mmol, 79% yield).

EXAMPLE 3

Synthesis of N-(4-Chlorophenyl)-N-phenylhydrazine

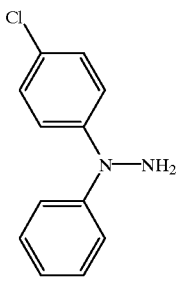

Phenylhydrazine (1.2 equiv., 0.6 mmol, 0.06 mL), 4-chlorobromobenzene (1.0 equiv., 0.5 mmol, 96 mg), Pd(OAc)$_2$ (0.05 equiv., 0.025 mmol, 6 mg), BINAP (0.05 equiv., 0.025 mmol, 16 mg), NaOtBu (1.4 equiv., 0.7 mmol, 67 mug) and diisopropylamine (2 mL) were added to an oven dried test tube which was capped with a septum and purged briefly with argon (~1 min.), and then heated to 80° C. under argon for 2.5 hours. The reaction was then cooled to room temperature, diluted with Et2O (2 mL), filtered through Celite and concentrated under vacuum. The crude mixture was purified by flash column chromatography (10% EtOAc/Hex) to give the title product as a yellow oil (42 mg, 0.19 mmol, 39% yield).

EXAMPLE 4

Synthesis of N-4-Benzotrifluoro-N-t-butyl carbazate

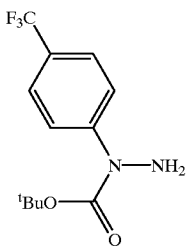

t-Butyl carbazate (1.2 equiv., 0.6 mmol, 79 mg), 4-bromobenzotrifluoride (1.0 equiv., 0.5 mmol, 0.07 mL), Pd(OAc)$_2$ (0.05 equiv., 0.025 mmol, 6 mg), BINAP (0.05 equiv., 0.025 mmol, 16 mg), Cs$_2$CO$_3$ (1.4 equiv., 0.7 mmol, 228 mg) and toluene (2 mL) were added to an oven dried test tube which was capped with a septum and purged briefly with argon (~1 min.), and then heated to 100° C. under argon for 8 hours. The reaction was then cooled to room temperature, diluted with Et$_2$O (2 mL), filtered through Celite and concentrated under vacuum. The crude mixture was purified by flash column chromatography (10% EtOAc/Hex) to give the title product as a yellow oil (50 mg, 0.18 mmol, 36% yield).

EXAMPLE 5

Synthesis of N,N-dimethyl-N'-phenylhydrazine

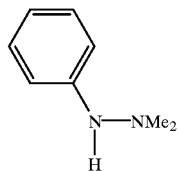

N,N-Dimethylhydrazine (2.0 equiv., 1.0 mmol, 0.075 mL), bromobenzene (1 equiv., 0.5 mmol, 0.05 mL), Pd$_2$(DBA)$_3$ (0.025 equiv., 0.0125 mmol, 12 mg), BINAP (0.05 equiv., 0.025 mmol, 16 mg), LiOtBu (1.2 equiv., 0.6 mmol, 48 mg) and toluene (5 mL) were added to an oven dried test tube which was capped with a septum and purged briefly with argon (~1 min.), and then heated to 80° C. under argon for 18 hours. The reaction was then cooled to room temperature, diluted with Et$_2$O (2 mL), filtered through Celite and concentrated under vacuum. The crude mixture was purified by flash column chromatography (10% EtOAc/Hex) to give the title product as a yellow oil (17 mg, 0.12 mmol, 24% yield).

EXAMPLE 6

Synthesis of Triphenylhydrazine

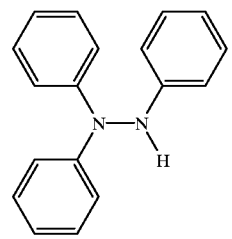

1,1-Diphenylhydrazine hydrochloride (1.2 equiv., 0.6 mmol, 135 mg), bromobenzene (1.0 equiv., 0.5 mmol, 0.05 mL), Pd(OAc)$_2$ (0.01 equiv., 0.005 mmol, 2 mg), BINAP (0.01 equiv., 0.005 mmol, 3 mg), and NaOtBu (2.8 equiv., 1.4 mmol, 134 mg) and toluene (3 mL) were added to an oven dried test tube which was capped with a septum and purged briefly with argon (~1 min.) and then heated to 80° C. for 4 hours. The reaction was then cooled to room temperature, diluted with Et$_2$O (2 mL), filtered through Celite and concentrated under vacuum. The crude mixture was purified by flash column chromatography (5% EtOAc/Hex) to give the title product as a white solid (123 mg, 0.47 mmol, 95% yield).

EXAMPLE 7

Synthesis of N-(4-Benzophenone)-N', N'-Diphenylhydrazine

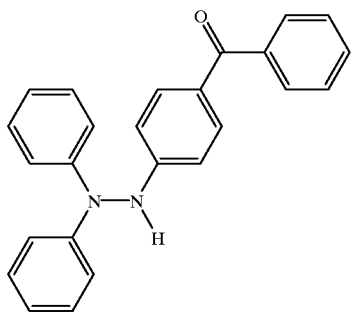

1,1-Diphenylhydrazine hydrochloride (1.2 equiv., 0.6 mmol, 135 mg), 4-bromobenzophenone (1.0 equiv., 0.5 mmol, 131 mg), Pd(OAc)2 (0.05 equiv, 0.025 mmol, 6 mg), BINAP (0.05 equiv., 0.025 mmol, 16 mg), and NaOtBu (2.8 equiv., 1.4 mmol, 134 mg) and diisopropylamine (2 mL) were added to an oven dried test tube which was capped with a septum and purged briefly with argon (~1 min.) and then heated to 80° C. for 2 hours. The reaction was then cooled to room temperature, diluted with Et$_2$O (2 mL), filtered through Celite and concentrated under vacuum. The crude mixture was purified by flash column chromatography (5% EtOAc/Hex) to give the title product as a white solid (141 mg, 0.39 mmol, 77% yield).

EXAMPLE 8
Synthesis of N,N-Diphenyl-N'-(2-chlorophenyl)hydrazine

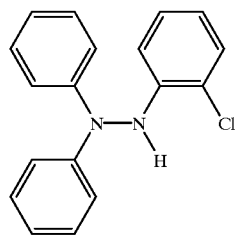

1,1-Diphenylhydrazine hydrochloride (1.2 equiv., 0.6 mmol, 135 mg), 2-chlorobromobenzene (1.0 equiv., 0.5 mmol, 0.06 mL), Pd(OAC)$_2$ (0.05 equiv, 0.025 mmol, 6 mg), BINAP (0.05 equiv., 0.025 mmol, 16 mg), and NaOtBu (1.4 equiv., 0.7 mmol, 67 mg) and diisopropylamine (2 mL) were added to an oven dried test tube which was capped with a septum and purged briefly with argon (~1 min.) and then heated to 80° C. for 5 hours. The reaction was then cooled to room temperature, diluted with Et$_2$O (2 mL), filtered through Celite and concentrated under vacuum. The crude mixture was purified by flash column chromatography (2% EtOAc/Hex) to give the title product as a white solid (109 mg, 0.37 mmol, 74% yield).

EXAMPLE 9
Synthesis of N,N'-Diphenyl-N-(4-benzotrifluoro)hydrazine

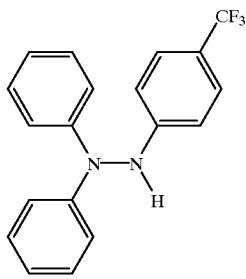

1,2-Diphenylhydrazine (1.2 equiv., 0.6 mmol, 110 mg), 4-bromobenzotrifluoride (1.0 equiv., 0.5 mmol, 0.07 mL), Pd(OAc)$_2$ (0.05 equiv, 0.025 mmol, 6 mg), BINAP (0.05 equiv., 0.025 mmol, 16 mg), and NaOtBu (1.4 equiv., 0.7 mmol, 67 mg) and diisopropylamine (2 mL) were added to a flame dried test tube which was capped with a septum and purged briefly with argon (~1 min.) and then heated to 80° C. for 5 hours. The reaction was then cooled to room temperature, diluted with Et$_2$O (2 mL), filtered through Celite and concentrated under vacuum. The crude mixture was purified by flash column chromatography (5% EtOAc/ Hex) to give the title product as a viscous yellow oil (90 mg, 0.27 mmol, 55% yield).

EXAMPLE 10
Synthesis of N',N'-Diethyl-N-phenylhydrazine

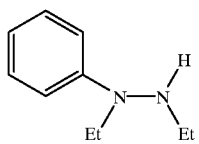

1,2-Diethylhydrazine dihydrochloride (1.2 equiv., 0.6 mmol, 97 mg), bromobenzene (1.0 equiv., 0.5 mmol, 0.05 mL), Pd(OAc)$_2$ (0.05 equiv, 0.025 mmol, 6 mg), BINAP (0.05 equiv., 0.025 mmol, 16 mg), and NaOtBu (3.8 equiv., 1.9 mmol, 183 mg) and diisopropylamine (2 mL) were added to a flame dried test tube which was capped with a septum and purged briefly with argon (~1 min.) and then heated to 80° C. for 4 hours. The reaction was then cooled to room temperature, diluted with Et$_2$O (2 mL), filtered through Celite and concentrated under vacuum. The crude mixture was purified by flash column chromatography (2% EtOAc/Hex) to give the title product as a viscous yellow oil (27 mg, 0.16 mmol, 33% yield).

EXAMPLE 11

N-(4-Phenylphenyl)cyclohexylhydrazone

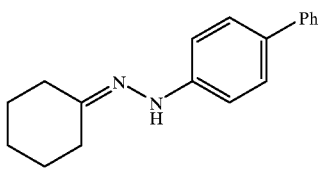

Cyclohexylhydrazone (1.0 equiv., 1.0 mmol, 112 mg), 4-bromobiphenyl (1.0 equiv., 1.0 mmol, 234 mg), Pd(OAc)$_2$ (0.05 equiv., 0.05 mmol, 11 mg), (S)-(–)-BINAP (0.05 equiv., 0.05 mmol, 31 mg), NaOt-Bu (1.4 equiv., 1.4 mmol, 134 mg), and toluene (0.2 M, 5 mL) were added to an oven dried test tube, which was then capped and briefly purged with argon and heated to 80° C. under argon for 9 hours The reaction mixture was then cooled to room temperature, diluted with Et$_2$O, filtered through Celite, and concentrated under vacuum. Purification by flash column chromatography (10% EtOAc/Hex) gave the title product as a white solid (72 mg, 0.27 mmol, 27% yield).

EXAMPLE 12

6-Phenyl-1,2,3,4-tetrahydrocarbazole

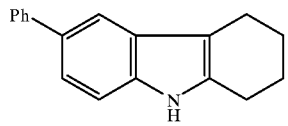

N-(4-Phenylphenyl) cyclohexylhydrazone (52 mg, 0.20 mmol) was heated to reflux in a 4% H$_2$SO$_4$/H$_2$O solution with 1 mL EtOH under argon for 4 hours. The reaction mixture was then cooled to room temperature, and neutralized with a saturated NaHCO$_3$ solution, and then extracted with CH$_2$Cl$_2$ (2×15 mL). The organic layer was then dried over Na$_2$SO$_4$, filtered and concentrated under vacuum. Purification by flash column chromatography (2% EtOAc/Hex) gave the title product as a white solid (22 mg, 0.09 mmol, 45% yield).

EXAMPLE 13

Synthesis of N-(4-Chlorophenyl)benzophenone hydrazone

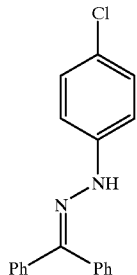

Benzophenone hydrazone (1 equiv., 10 mmol, 2.04 g), 4-chlorobromobenzene (1.0 equiv., 10 mmol, 1.915 g), Pd(OAc)$_2$ (0.01 equiv., 0.1 mmol, 23 mg), BINAP (0.01 equiv., 0.1 mmol, 63 mg), and toluene (5 mL) were added to an oven dried Schlenk flask and stirred at room temperature for 2 minutes, NaOtBu (1.4 equiv., 14 mmol, 1.345 g) and an additional 5 mL of toluene were then added. The flask was capped with a septum and purged briefly with argon (~1 min.) and heated to 80° C. under argon for 13 hours. The reaction mixture was then cooled to room temperature, diluted with Et$_2$O (10 mL), and concentrated under vacuum to give the crude product as a brown solid. Recrystallization of the crude product from hot isopropanol (100 mL) gave the desired product as a yellow solid (1.971 g, 6.4 mmol, 64% yield). The mother liquor was concentrated under vacuum and purified by column chromatography (5% EtOAc/Hex) to give an additional 550 mg of the desired product (1.79 mmol, 18% yield), to give an 82% overall yield of the title product.

EXAMPLE 14

Synthesis of 6-Chloro-1,2,3,4-tetrahydrocarbazole

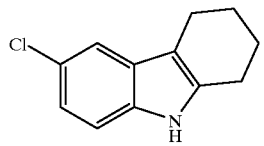

N-(4-Chlorophenyl)benzophenone hydrazone (1.0 equiv., 0.5 mmol, 153 mg), cyclohexanone (1.5 equiv., 0.75 mmol, 0.078 mL), and TsOH.H$_2$O (2 equiv., 1.0 mmol, 190 mg) were dissolved in ethanol (3 mL) and heated to reflux for 41 hours. The reaction mixture was then cooled to room temperature, diluted with Et$_2$O (5 mL), neutralized with a saturated NaHCO$_3$ solution, and extracted with Et$_2$O (3×10 mL). The organic extracts were then dried over K$_2$CO$_3$, filtered and concentrated under vacuum. Purification by flash column chromatography (10% EtOAc/Hex) gave the title product as a white solid (94 mg, 0.46 mmol, 91% yield).

EXAMPLE 15

Synthesis of N-Benzyl-6-chloro-1,2,3,4-tetrahydrocarbazole

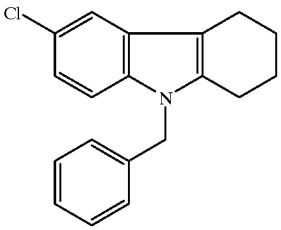

4-Chlorophenyl benzophenone hydrazone (1 equiv., 1 mmol, 306 mg) was dissolved in 5 mL dry Et$_2$O in a flame dried flask under argon. n-BuLi (1.1 equiv., 1.1 mmol, 1.58 M in hexane, 0.69 mL) was then added in a drop wise fashion and the solution was then stirred at room temperature for 10 minutes. Distilled tetramethylethylenediamine (TMEDA, 2.2 equiv., 2.2 mmol, 0.33 mL) was then added, followed by benzyl bromide (1.2 equiv., 1.2 mmol, 0.21 mL). After 3 hours the solution was quenched with an aqueous NH$_4$Cl solution, extracted with Et$_2$O (3×10 mL), the Et$_2$O extracts were dried over K$_2$CO$_3$, filtered and concentrated under vacuum to give N-benzyl-N4-chlorophenylbenzophenone hydrazone as a yellow oil which was used without further purification. This crude product was dissolved in EtOH (3 mL), TsOH.H$_2$O (380 mg) was then added and the reaction mixture was heated to reflux for 23 hours. The reaction mixture was then cooled to room temperature, neutralized with a saturated NaHCO$_3$ solution, extracted with Et$_2$O (2×10 mL) and then with EtOAc (2×10 mL). The combined organic extracts were then dried over K$_2$CO$_3$, filtered and concentrated to give the crude product as a brown oil. Purification by flash column chromatography (2 % EtOAc/Hex) afforded the title product as a pale yellow oil which solidified on standing (269 mg, 0.91 mmol, 91% yield).

EXAMPLE 16

Synthesis of 5-Chloro-3-pentylindole

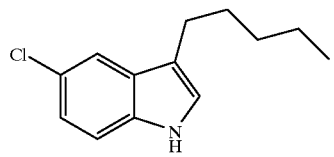

N-(4-Chlorophenyl)benzophenone hydrazone (1.0 equiv., 0.5 mmol, 153 mg), heptanal (5 equiv., 2.5 mmol, 0.29 mL), and TsOH.H$_2$O (10 equiv., 5 mmol, 951 mg) were dissolved in THF (10 mL) and heated to reflux for 41 hours. The reaction mixture was then cooled to room temperature, diluted with Et$_2$O (5 mL), neutralized with a saturated NaHCO$_3$ solution, and extracted with Et$_2$O (3×10 mL). The organic extracts were then dried over K$_2$CO$_3$, filtered and concentrated under vacuum. Purification by two flash column chromatographies (10% EtOAc/Hex) gave the title product as a yellow oil (29 mg, 0.13 mmol, 26% yield).

EXAMPLE 17

Synthesis of N-(3,4-Dimethoxyphenyl)benzophenone hydrazone

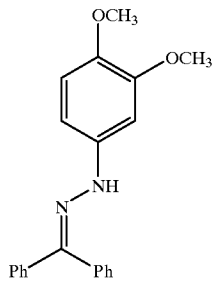

Benzophenone hydrazone (1 equiv., 10 mmol, 2.04 g), 4-bromoveratole (1.0 equiv., 10 mmol, 1.44 mL), Pd(OAc)$_2$ (0.05 equiv., 0.5 mmol, 112 mg), BINAP (0.05 equiv., 0.5 mmol, 311 mg), and toluene (10 mL) were added to an oven dried Schlenk flask and stirred at room temperature for 2 minutes, NaOtBu (1.4 equiv., 14 mmol, 1.345 g) and an additional 10 mL of toluene were then added. The flask was capped with a septum and purged briefly with argon (~1 min.) and heated to 80° C. under argon for 22 hours. The reaction mixture was then cooled to room temperature, diluted with Et$_2$O (10 mL), and concentrated under vacuum to give the crude product as a brown oil. Purification of the crude mixture by flash column chromatography (15% EtAOc/Hex) gave the title product as a yellow solid (2.161 g, 6.5 mmol, 65% yield).

EXAMPLE 18

Synthesis of 5,6-Dimethoxy-2-methyl-3-propylindole

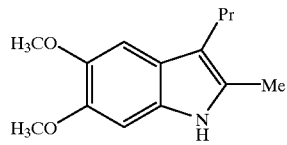

N-(3,4-Dimethoxyphenyl)-benzophenone hydrazone (1.0 equiv., 0.32 mmol, 105 mg), 2-hexanone (5 equiv., 1.58 mmol, 0.19 mL), and TsOH.H$_2$O (10 equiv., 3.2 mmol, 609 mg) were dissolved in THF (10 mL) and heated to reflux for 67 hours. The reaction mixture was then cooled to room temperature, diluted with Et$_2$O (5 mL), neutralized with a saturated NaHCO$_3$ solution, and extracted with Et$_2$O (3×10 mL). The organic extracts were then dried over K$_2$CO$_3$, filtered and concentrated under vacuum. Purification by flash column chromatography (20% EtOAc/Hex) gave the title product as a yellow oil (60 mg, 0.26 mmol, 80% yield).

EXAMPLE 19

Synthesis of N-(1-Naphthyl)benzophenone hydrazone

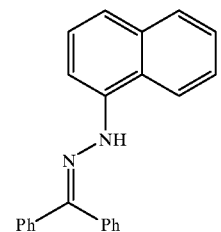

Benzophenone hydrazone (1 equiv., 10 mmol, 2.04 g), 1-bromonaphthalene (1.0 equiv., 10 mmol, 1.39 mL), Pd(OAc)$_2$ (0.01 equiv., 0.1 mmol, 23 mg), BINAP (0.01 equiv., 0.1 mmol, 63 mg), and toluene (10 mL) were added to an oven dried Schlenk flask and stirred at room temperature for 2 minutes, NaOtBu (1.4 equiv., 14 mmol, 1.345 g) and an additional 10 mL of toluene were then added. The flask was capped with a septum and purged briefly with argon (~1 min.) and heated to 80° C. under argon for 4.5 hours. The reaction mixture was then cooled to room temperature, diluted with Et$_2$O (10 mL), and concentrated under vacuum to give the crude product as a brown solid. Recrystallization of the crude product from hot ethanol (150 mL) gave the desired product as a red solid (1.6939 g, 5.26 mmol, 53% yield). The mother liquor was concentrated until the solution became cloudy, and then heated until the solution became clear, filtered and cooled to –4° C. for 12 hours. The resulting crystals were filtered to give an additional 1.062 g of the title product as an orange/red solid (3.3 mmol, 33% yield), to give a 85% overall yield of the desired product.

EXAMPLE 20

Synthesis of 3-Ethoxyacety1–2-methylbenz[g]indole

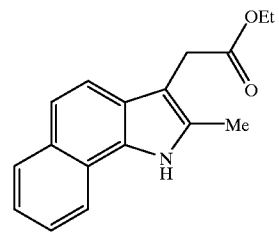

N-(1-Naphthyl)-benzophenone hydrazone (1.0 equiv., 1.0 mmol, 322 mg), levulinic acid (1.5 equiv., 1.5 mmol, 0.18 mL), and TsOH.H$_2$O (2 equiv., 2 mmol mmol, 380 mg) were dissolved in ethanol (10 mL) and heated to reflux for 15 hours. The reaction mixture was then cooled to room temperature, diluted with Et$_2$O (5 mL), neutralized with a saturated NaHCO$_3$ solution, and extracted with Et$_2$O (3×10 mL). The organic extracts were then dried over Na$_2$SO$_4$, filtered and concentrated under vacuum. Purification by flash column chromatography (20% EtOAc/Hex) gave the title product as a yellow oil (238 mg, 0.89 mmol, 89% yield).

EXAMPLE 21

Synthesis of N-(3,5-Dimethylphenyl)-N-(4-benzotrifluoro)benzophenone hydrazone

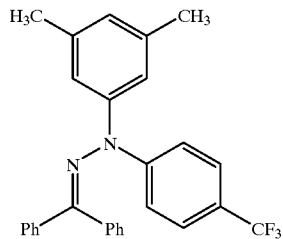

N-(3,5-Dimethylphenyl)benzophenone hydrazone (1.0 equiv., 0.5 mmol, 150 mg), 4-bromobenzotrifluoride (1.0 equiv., 0.5 mmol, 0.07 mL), Pd(OAc)$_2$ (0.01 equiv, 0.005 mmol, 2 mg), DPPF (0.01 equiv, 0.005 mmol, 3 mg), and toluene (1 mL) were added to an oven dried test tube and stirred at room temperature for 2 minutes. NaOtBu (1.4 equiv., 0.7 mmol, 67 mg) and an additional 1 mL toluene were then added. The test tube was then capped with a septum, briefly purged with argon (~1 min.) and then heated to 100° C. under argon for 14 hours. The reaction solution was then cooled to room temperature, diluted with Et$_2$O, filtered through Celite, and concentrated under vacuum to give the crude product as a brown oil. Purification by flash column chromatography (2% EtOAc/Hex) gave the title product in approximately 72% purity as determined by $^1$H NMR (158 mg, ~0.26 mmol, ~51% yield).

EXAMPLE 22

Synthesis of N-(4-Benzotrifluoro)-6,8-dimethyl-2,3,4,5-tetrahydrocarbazole

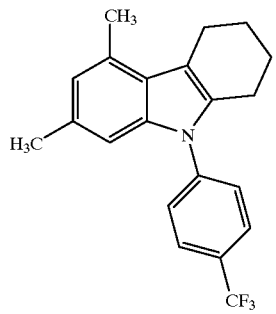

N-(3,5-Dimethylphenyl)-N-(4-benzotrifluoro)-benzophenone hydrazone (1 equiv., ~0.26 mmol, ~51% yield), cyclohexanone (1.5 equiv., 0.75 mmol, 0.078 mL), TSOH.H$_2$O (2 equiv., 1.0 mmol, 190 mg), and ethanol (3 mL) were heated to reflux for 14 hours. The reaction solution was then cooled to room temperature, neutralized with a saturated NaHCO$_3$ solution, extracted with Et$_2$O (3×10 mL), and dried over K$_2$CO$_3$, and concentrated under vacuum. Purification by flash column chromatography (2% EtOAc/Hex) gave the impure title product (73 mg, ~0.21 mmol, a82% yield).

EXAMPLE 23

Synthesis of N-(3,5-Dimethylphenyl)-N-(4-phenylphenyl)benzophenone hydrazone

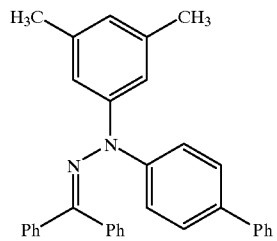

N-(3,5-Dimethylphenyl)benzophenone hydrazone (1.0 equiv., 0.5 mmol, 150 mg), 4-bromobiphenyl (1.0 equiv., 0.5 mmol, 117 mg), Pd(OAc)$_2$ (0.01 equiv, 0.005 mmol, 2 mg), DPE-phos (0.01 equiv, 0.005 mmol, 3 mg), and toluene (1 mL) were added to an oven dried test tube and stirred at room temperature for 2 minutes. NaOtBu (1.4 equiv., 0.7 mmol, 67 mg) and an additional 1 mL toluene were then added. The test tube was then capped with a septum, briefly purged with argon (~1 min.) and then heated to 100° C. under argon for 14 hours. The reaction solution was then cooled to room temperature, diluted with Et$_2$O, filtered through Celite, and concentrated under vacuum to give the crude product as a brown oil. Purification by flash column chromatography (2% EtOAc/Hex) gave the title product as a yellow solid (149 mg, 0.33 mmol, 66% yield).

All publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for the vinylation of hydrazines, hydrazones, hydroxylamines and oximes, comprising reacting a base, a transition metal catalyst, a substrate vinyl compound comprising an activated carbon bearing a leaving group, and a hydrazine, hydrazone, hydroxylamine or oxime under conditions suitable for the transition metal catalyst to effect the formation of a carbon-heteroatom bond between the activated carbon of said substrate vinyl compound and a heteroatom of said hydrazine, hydrazone, hydroxylamine or oxime.

2. The method of claim 1, wherein the transition metal of the transition metal catalyst is selected from the group comprising Fe, Ru, Co, Rh, Ir, Ni, Pd, Pt, and Cu.

3. The method of claim 1, wherein the transition metal catalyst is present in substoichiometric quantities relative to the limiting reagent among said activated aryl or vinyl compound, and said hydrazine, hydrazone, hydroxylamine or oxime.

4. The method of claim 2, wherein the transition metal catalyst is present in substoichiometric quantities relative to the limiting reagent among said activated aryl or vinyl compound, and said hydrazine, hydrazone, hydroxylamine or oxime.

5. The method of claim 1, wherein the transition metal catalyst is present in less than or equal to 50 mol % relative to the limiting reagent among said activated aryl or vinyl compound, and said hydrazine, hydrazone, hydroxylamine or oxime.

6. The method of claim 2, wherein the transition metal catalyst is present in less than or equal to 50 mol % relative to the limiting reagent among said activated aryl or vinyl compound, and said hydrazine, hydrazone, hydroxylamine or oxime.

7. The method of claim 1, wherein the transition metal catalyst is present in less than or equal to 10 mol % relative to the limiting reagent among said activated aryl or vinyl compound, and said hydrazine, hydrazone, hydroxylamine or oxime.

8. The method of claim 2, wherein the transition metal catalyst is present in less than or equal to 10 mol % relative to the limiting reagent among said activated aryl or vinyl compound, and said hydrazine, hydrazone, hydroxylamine or oxime.

9. The method of claim 1, wherein the transition metal catalyst is present in less than or equal to 5 mol % relative to the limiting reagent among said activated aryl or vinyl compound, and said hydrazine, hydrazone, hydroxylamine or oxime.

10. The method of claim 2, wherein the transition metal catalyst is present in less than or equal to 5 mol % relative to the limiting reagent among said activated aryl or vinyl compound, and said hydrazine, hydrazone, hydroxylamine or oxime.

11. The method of claim 1, wherein the transition metal catalyst is present in less than or equal to 2 mol % relative to the limiting reagent among said activated aryl or vinyl compound, and said hydrazine, hydrazone, hydroxylamine or oxime.

12. The method of claim 2, wherein the transition metal catalyst is present in less than or equal to 2 mol % relative to the limiting reagent among said activated aryl or vinyl compound, and said hydrazine, hydrazone, hydroxylamine or oxime.

13. The method of claim 1, wherein the activated group on the aromatic compound is selected from the group comprising halide s and sulfonates.

14. The method of claim 13, wherein the activated group on the aromatic compound is selected from the group comprising chloride, bromide, iodide, tosylate, mesylate, triflate, and nonaflate.

15. The method of claim 2, wherein the activated group on the aromatic compound is selected from the group comprising halides and sulfonates.

16. The method of claim 15, wherein the activated group on the aromatic compound is selected from the group comprising chloride, bromide, iodide, tosylate, mesylate, triflate, and nonaflate.

17. The method of claim 1, wherein the hydrazine, hydrazone, hydroxylamine or oxime is selected from the group comprising hydrazine, alkyl and aryl hydrazines, 1,1- and 1,2-dialkyl and diaryl hydrazines, 1,1- and 1,2-alkyl aryl hydrazines, 1,1,2-trialkyl and triaryl hydrazines, 1,1,2-dialkyl aryl and alkyl diaryl hydrazines, aldehyde and ketone hydrazones, N-alkyl and N-aryl aldehyde and ketone hydrazones, hydroxylamine, O-alkyl and O-aryl hydroxylamines, N-alkyl and N-aryl hydroxylamines, N,O-dialkyl and N,O-diaryl hydroxylamines, N,O-alkyl aryl hydroxylamines, N,N-dialkyl and N,N-diaryl hydroxylamines, and N,N-alkyl aryl hydroxylamines, and aldehyde and ketone oximes.

18. The method of claim 2, wherein the hydrazine, hydrazone, hydroxylamine or oxime is selected from the group comprising hydrazine, alkyl and aryl hydrazines, 1,1- and 1,2-dialkyl and diaryl hydrazines, 1,1- and 1,2-alkyl aryl hydrazines, 1,1,2-trialkyl and triaryl hydrazines, 1,1,2-dialkyl aryl and alkyl diaryl hydrazines, aldehyde and ketone hydrazones, N-alkyl and N-aryl aldehyde and ketone hydrazones, hydroxylamine, O-alkyl and O-aryl hydroxylamines, N-alkyl and N-aryl hydroxylamines, N,O-dialkyl and N,O-diaryl hydroxylamines, N,O-alkyl aryl hydroxylamines, N,N-dialkyl and N,N-diaryl hydroxylamines, and N,N-alkyl aryl hydroxylamines, and aldehyde and ketone oximes.

19. The method of claim 1, represented by scheme 5:

Scheme 5

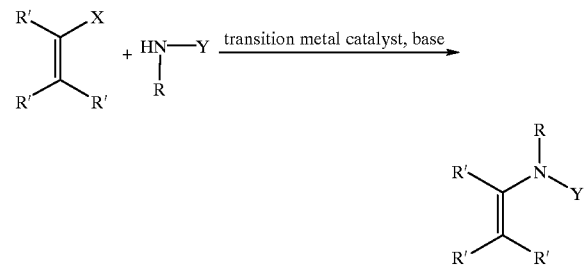

wherein
X represents an activated group which can be replaced by a nucleophilic nitrogen in a transition metal-catalyzed vinylation reaction;

Y represents $NR_2$, $OR$, $N=CR_2$, $N(R)C(O)NR_2$;

R represents independently for each occurrence H, alkyl, alkenyl, formyl, acyl, sulfonyl, or $-(CH_2)_m-R_8$;

R' represents independently for each occurrence H, halogen, lower alkyl, lower alkenyl, lower alkynyl, carbonyl, ester, carboxylate, formate, thiocarbonyl, thiolester, thiolcarboxylate, thiolformate, ketone, aldehyde, amino, acylamino, amido, amidino, cyano, nitro, azido, sulfonyl, sulfonyl, sulfoxido, sulfate, sulfonate, sulfamoyl, sulfonamido, phosphoryl, phosphonate, phosphinate, $-(CH_2)_m-R_8$, $-(CH_2)_m-O-$lower alkyl, $-(CH_2)_m-O-$lower alkenyl, $-(CH_2)_m-O-(CH_2)_n-R_8$, $-(CH_2)_m-SH$, $-(CH_2)_m-S-$lower alkyl, $-(CH_2)_m-S-$lower alkenyl, $-(CH_2)_m-S-(CH_2)_nR_8$, or a solid or polymeric support;

$R_8$ represnts independently for each occurrence aryl, cycloalkyl, cycloalkenyl, heterocycle or polycycle; and n and m are integers independently for each occurrence selected from the range of 0 to 8 inclusive.

20. The method of claim 1, represented by scheme 6:

Scheme 6

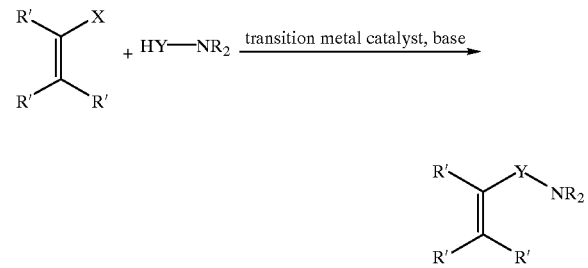

wherein
X represents an activated group, which can be replaced by Y in a transition metal- catalyzed vinylation reaction;

Y represents O, S, or Se;

R independently for each occurrence is absent or represents H, alkyl, alkenyl, alkylidene, formyl, acyl, sulfonyl, or —$(CH_2)_m$—$R_8$;

R' represents independently for each occurrence H, halogen, lower alkyl, lower alkenyl, lower alkynyl, carbonyl, ester, carboxylate, formate, thiocarbonyl, thiolester, thiolcarboxylate, thiolformate, ketone, aldehyde, amino, acylamino, amido, amidino, cyano, nitro, azido, sulfonyl, sulfoxido, sulfate, sulfonate, sulfamoyl, sulfonamido, phosphoryl, phosphonate, phosphinate, —$(CH_2)_m$—$R_8$, —$(CH_2)_m$—OH, —$(CH_2)_m$—O—lower alkyl, —$(CH_2)_m$—O—lower alkenyl, —$(CH_2)_m$—O—$(CH_2)_m$—SH, —$(CH_2)_m$—S—lower alkyl, —$(CH_2)_m$—S—lower alkenyl, —$(CH_2)_m$—S—$(CH_2)_n$—$R_8$, or a solid or polymeric support;

$R_8$ represents independently for each occurrence aryl, cycloalkyl, cycloalkenyl, heterocycle or polycycle; and n and m are integers independently for each occurrence selected from the range of 0 to 8 inclusive.

* * * * *